United States Patent [19]

Hyzak et al.

[11] Patent Number: 4,613,358
[45] Date of Patent: Sep. 23, 1986

[54] HERBICIDE COMPOSITIONS OF EXTENDED SOIL LIFE

[75] Inventors: Daniel L. Hyzak, Austin, Tex.; Reed A. Gray, Saratoga, Calif.

[73] Assignee: Stauffer Chemical Co., Westport, Conn.

[21] Appl. No.: 592,687

[22] Filed: Mar. 23, 1984

Related U.S. Application Data

[63] Continuation-in-part of Ser. No. 496,705, May 20, 1983, abandoned, which is a continuation of Ser. No. 350,782, Feb. 22, 1983, abandoned, which is a continuation of Ser. No. 163,651, Jun. 27, 1980, abandoned.

[51] Int. Cl.$^4$ .............................................. A01N 25/22
[52] U.S. Cl. ............................................ 71/100; 71/87
[58] Field of Search ................................... 71/87, 100

[56] References Cited

U.S. PATENT DOCUMENTS

| | | | |
|---|---|---|---|
| 2,913,327 | 11/1959 | Tilles et al. | 71/100 |
| 3,336,188 | 8/1967 | Tolkmith et al. | 424/200 |
| 3,450,713 | 6/1969 | Tolkmith et al. | 424/200 |
| 3,932,632 | 1/1976 | Adolphi et al. | 424/213 |
| 3,938,986 | 2/1976 | Pray | 71/100 |
| 4,047,928 | 9/1977 | Bond et al. | 71/88 |

FOREIGN PATENT DOCUMENTS

| | | |
|---|---|---|
| 2652467 | 5/1978 | Fed. Rep. of Germany . |
| 964793 | 7/1964 | United Kingdom . |

OTHER PUBLICATIONS

Nobekawa et al, I Chem. Abst., vol. 89 (1978) 108735v.
Nobekawa et al, II, Chem. Abst. vol. 89 (1978) 108736w.
Nasb. Weed. Sci, vol. 10 No. 1 (1968), pp. 74–77.
Byers et al. Chem. Abst., vol. 87 (1977), 128777x.

*Primary Examiner*—Catherine L. Mills
*Attorney, Agent, or Firm*—Harry A. Pacini; Leona L. Lauder

[57] ABSTRACT

The soil life of herbicidally active thiolcarbamates is extended by certain organophosphorus compounds having the formula

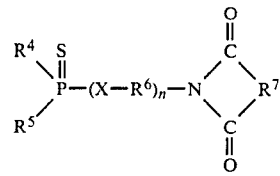

in which $R^4$ is selected from the group consisting of $C_1$–$C_4$ alkyl and $C_1$–$C_4$ alkoxy; $R^5$ is selected from the group consisting of $C_1$–$C_4$ alkoxy, $C_1$–$C_4$ alkylthio, $C_2$–$C_4$ alkenoxy, and $C_2$–$C_4$ alkenylthio; $R^6$ is selected from the group consisting of phenyl, $C_1$–$C_4$ alkylene, and $C_2$–$C_4$ alkylthioalkylene; $R^7$ is either phenyl or cyclohexenyl; X is oxygen or sulfur, and n is zero or one.

11 Claims, No Drawings

HERBICIDE COMPOSITIONS OF EXTENDED SOIL LIFE

CROSS REFERENCE TO RELATED APPLICATIONS

This is a continuation-in-part application of application U.S. Ser. No. 496,705, filed May 20, 1983, now abandoned; which in turn is a continuation of application Ser. No. 350,782, filed Feb. 22, 1983, now abandoned; which in turn is a continuation of application Ser. No. 163,651, filed June 27, 1980, now abandoned.

BACKGROUND OF THE INVENTION

This invention relates to herbicidal compositions and methods of use. In particular, this invention relates to herbicidal compositions comprising an herbicidally active thiolcarbamate in combination with certain organophosphorus compounds, the latter serving to prolong the effectiveness of a single application of the thiolcarbamate in controlling undesired plant growth.

Thiolcarbamates are well known in the agricultural art as herbicides useful for weed control in crops such as corn, potatoes, beans, beets, spinach, tobacco, tomatoes, alfalfa, rice and others. Thiolcarbamates are primarily used in pre-emergence application, and are particularly effective when incorporated into the soil polar to the planting of the crop. The concentration of the thiolcarbamate in the soil is greatest immediately after application of the compound. How long thereafter the initial concentration is retained depends in large part on the particular soil used. The rate at which the thiolcarbamate concentration declines following its application varies from one type of soil to the next. This is evident both in the observable extent of weed control and in the detectable presence of undegraded thiolcarbamate remaining in the soil after considerable time has elapsed.

It is therefore an object of this invention to increase the soil persistence of thiolcarbamate herbicides and thus improve their herbicidal effectiveness.

BRIEF DESCRIPTION OF THE INVENTION

It has now been discovered that the soil persistence of certain herbicidally active thiolcarbamates is significantly extended by the further addition to the soil of certain extender compounds in the form of organophosphorus compounds, which have little or no herbicidal activity of their own and do not decrease the herbicidal activity of the thiolcarbamate. This improvement in the soil persistence of thiolcarbamates manifests itself in a variety of ways. It can be shown, for example, by soil analyses taken at regular intervals, that the rate of decrease of the thiolcarbamate content of the soil is substantially lessened. Improved soil persistence can also be shown by improvements in herbicidal efficacy, as evidenced by a higher degree of weed injury brought about when the extender compound increases the soil persistence of the thiolcarbamate, prolonging its effective life.

In particular, this invention relates to a novel herbicidal composition comprising (a) an herbicidally effective amount of a thiolcarbamate having the formula $$R^1-S-\underset{\underset{O}{\|}}{C}-N\underset{R^3}{\overset{R^2}{\diagup}}$$

in which $R^1$, $R^2$, and $R^3$ are independently $C_2$–$C_4$ alkyl with the proviso that wherein $R^1$ is ethyl and $R^2$ is propyl, $R^3$ is other than propyl; and (b) an amount of an organophosphorus compound sufficient to extend the soil life of said thiolcarbamate, said organophosphorus compound having the formula $$\underset{R^5}{\overset{R^4}{\diagdown}}\underset{\|}{\overset{S}{P}}-(X-R^6)_n-N\underset{\underset{\|}{O}}{\overset{\overset{\|}{O}}{\diagup\diagdown}}R^7$$

in which
$R^4$ is selected from the group consisting of $C_1$–$C_4$ alkyl and $C_1$–$C_4$ alkoxy;
$R^5$ is selected from the group consisting of $C_1$–$C_4$ alkoxy, $C_1$–$C_4$ alkylthio, $C_2$–$C_4$ alkenoxy, and $C_2$–$C_4$ alkenylthio;
$R^6$ is selected from the group consisting of phenyl, $C_1$–$C_4$ alkylene, and $C_2$–$C_4$ alkylthioalkylene;
$R^7$ is either phenyl or cyclohexenyl
X is oxygen or sulfur, and
n is zero or one.

When $R^7$ is phenyl, the extender compounds are phthalimide-containing compounds.

When $R^7$ is cyclohexenyl, the extender compounds are tetrahydrophthalimide-containing compounds.

Within the scope of the present invention, certain embodiments are preferred, namely:

In the thiolcarbamate formula, when $R^1$ is ethyl, $R^2$ and $R^3$ are each preferably isobutyl; and when $R^1$ is propyl, $R^2$ and $R^3$ are each preferably propyl. However, when the extender is N-(4 O,O'-diethylmonothiophosphorophenyl) $\Delta^4$ tetrahydrophthalmide, the thiolcarbamate is other than S-ethyl N,N-diisobutylthiolcarbamate.

In the organophosphorus compound formulas, it is preferred that:
$R^4$ is either $C_1$–$C_4$ alkyl or $C_1$–$C_4$ alkoxy;
$R^5$ is either $C_1$–$C_4$ alkoxy, $C_1$–$C_4$ alkylthio, or $C_2$–$C_4$ alkenylthio;
$R^6$ is $C_1$–$C_2$ alkylene, phenyl, or $C_2$–$C_2$ alkylthioalkylene;
$R^7$ is phenyl or 3,4-cyclohexenyl; and
X and n are defined as above.

This invention further relates to a method of controlling undesirable vegetation comprising applying the above composition to the locus where control is desired.

The terms "alkyl," "alkoxy," and "alkynylthio" are used herein in their normal meanings and are intended to include both straight-chain and branched-chain groups. The term "alkylene" is used to denote a saturated bivalent hydrocarbon radical consisting of the —$CH_2$— group or multiples thereof, optionally substituted with alkyl groups and thereby including both straight-chain and branched-chain groups. Examples are —$CH_2$—, —$CH_2CH_2$—, —$CH_2CH_2CH_2$—, —CH(CH$_3$)CH$_2$—, —CH$_2$CH(CH$_3$)CH$_2$—, etc. All carbon atom ranges are inclusive of their upper and lower limits.

The term "herbicide", as used herein, means a compound or composition which controls or modifies the growth of plants. By the term "herbicidally effective amount" is meant any amount of such compound or composition which causes a modifying effect upon the growth of plants. By "plants" is meant germinant seeds, emerging seedlings and established vegetation, including roots and above-ground portions. Such controlling or modifying effects include all deviations from natural development, such as killing, retardation, defoliation, regulation, stunting, tillering, stimulation, leaf burn, dwarfing and the like.

The phrase "to extend the soil life of said thiolcarbamate" as used herein means to retard the rate at which molecules of thiolcarbamate are broken down into decomposition products when in contact with soil and/or to prolong the period of time following application in which herbicidal effects can be observed. This applies both to field sites where repeated applications of thiolcarbamates have resulted in decreasing herbicidal effectiveness, and to field sites where a decline in activity is detected over time regardless of the prior history of herbicidal applications. An extended soil life can be manifest in a slower rate of decline of weed-killing activity, or an increased half-life of thiolcarbamate concentration in the soil. Other techniques of determining soil life are readily apparent to one skilled in the art.

DETAILED DESCRIPTION OF THE INVENTION

The thiolcarbamates within the scope of the present invention can be prepared by the process described in U.S. Pat. No. 2,913,327 (Tilles et al., Nov. 17, 1959). The organophosphorus compounds can be prepared by the process described in U.S. Pat. No. 3,336,188 (Tolkmith et al., Aug. 5, 1967) and U.S. Pat. No. 3,450,713 (Tolkmith et al., June 17, 1969). Some of the compounds can also be prepared by analogous reactions to those described in U.S. Pat. No. 4,058,535 (Fancher, Nov. 15, 1977).

The objects of the present invention are achieved by applying the organophosphorus extender compound to the soil at an agricultural field site in conjunction with the thiolcarbamate herbicide. The two compounds can be applied simultaneously in a single mixture or in separate formulations, or they can be applied in succession, with either one following the other. In successive application, it is preferable to add the compounds as close in time as possible.

The herbicide extending effect is operable over a wide range of ratios of the two compounds. It is most convenient, however, to apply the compounds at a ratio of about 1:1 to about 20:1 (herbicide/extender) on a weight basis, preferably about 1:1 to about 10:1, and most preferably about 1:1 to about 5:1.

Thiolcarbamate herbicides useful in the present invention include S-ethyl diisobutylthiolcarbamate, S-n-propyl di-n-propylthiolcarbamate, and S-n-propyl ethyl-n-butylthiolcarbamate.

The variety of crops on which the present composition is useful can be significantly broadened by the use of an antidote to protect the crop from injury and render the composition more selective against weeds.

For antidote descriptions and methods of use, reference is made to U.S. Pat. No. 3,959,304, issued to E. G. Teach on May 25, 1976; U.S. Pat. No. 3,989,503, issued to F. M. Pallos et al. on Nov. 2, 1976; U.S. Pat. No. 4,021,224, issued to F. M. Pallos et al. on May 3, 1977; U.S. Pat. No. 3,131,509 issued to O. L. Hoffman on May 5, 1964; and U.S. Pat. No. 3,564,768, issued to O. L. Hoffman on Feb. 3, 1971.

Examples of useful antidotes include acetamides such as N,N-diallyl-2,2-dichloroacetamide and N,N-diallyl-2-chloroacetamide, oxazolidines such as 2,2,5-trimethyl-N-dichloroacetyl oxazolidine and 2,2-spirocyclohexyl-N-dichloroacetyl oxazolidine, and 1,8-naphthalic anhydride. For maximum effect, the antidote is present in the composition in a non-phytotoxic, antidotally effective amount. By "non-phytotoxic" is meant an amount which causes at most minor injury to the crop. By "antidotally effective" is meant an amount which substantially decreases the extent of injury caused by the herbicide to the crop. The preferred weight ratio of herbicide to antidote is about 0.1:1 to about 30:1. The most preferred range for this ratio is about 3:1 to about 20:1.

The following examples are offered to illustrate the utility of the present invention, and are intended neither to limit nor define the invention in any manner.

EXAMPLES

This example shows, by soil analysis, the effectiveness of the compounds of the present invention in extending the soil life of the thiolcarbamate herbicides. The herbicide used in these tests was S-ethyl di-n-propylthiolcarbamate, commonly known as EPTC. The soil was a sandy loam soil obtained from Sunol, Calif., containing approximately (on a weight basis) 64% sand, 29% silt, and 7% clay, determined by mechanical means. The total organic content of the soil was approximately 4% by weight and the pH was 6.8, both determined by chemical analysis.

The test procedure involved an initial pre-treatment of the soil to simulate field conditions where the soil had been previously treated with EPTC, followed by a soil persistence test, as described below.

A. Soil Pre-Treatment

An emulsion was prepared by diluting an emulsifiable liquid concentrate containing 6 lb/gal (0.72 kg/l) of the thiolcarbamate in 100 ml of water, such that the concentration of thiolcarbamate in the resulting emulsion was 4000 mg/l. Five ml of this emulsion was then added to 10 lb (4.54 kg) of soil and the mixture was mixed in a rotary mixer for 10–20 seconds.

Round plastic containers, 9 inches (22.9 cm) in diameter by 9 inches (22.9 cm) deep, were then filled with the sandy loam soil, which was tamped and leveled with a row marker to impress three rows across the width of each container. Two rows were seeded with DeKalb XL-45A corn *Zea mays* (L.), and one row was seeded with barnyardgrass *Echinochloa crusgalli* (L.). Sufficient seeds were planted to produce several seedlings per row. The containers were then placed in a greenhouse maintained at 20° C. to 30° C. and watered daily by sprinkler.

Five weeks after treatment, the soil was allowed to dry out and the plant foliage was removed. The soil was then passed through a 0.25 inch (0.64 cm) screen, followed by a 2 millimeter (mm) screen, to remove plant roots and clods.

B. Soil Persistence Test

A 100-gram quantity (air-dry basis) of the pre-treated soil was placed in an 8-ounce (0.25 liter) wide-mouth glass bottle. The same emulsifiable concentrate described in Part A above was appropriately diluted in water such that a 5-ml portion added to the soil would produce a herbicide concentration of 6 ppm (weight) in the soil. This is equivalent to an application rate of 6 pounds per acre (6.7 kilograms per hectare) in a field where the herbicide is incorporated into the soil through a depth of about 2 inches (5.08 cm) soon after application. A selected extender compound in technical (nonformulated) form was then diluted in an acetonewater mixture such that a one-ml portion added to the soil would produce a concentration of 4 ppm by weight, equivalent to 4 pounds per acre (4.5 kilograms per hectare). On these bases, the herbicide and extender were added to the bottle containing the soil. The bottle was then sealed with a lid and shaken manually for approximately 15 minutes.

Following such treatment, the soil was moistened with 20 ml deionized water. The bottle was then covered with a watch glass to maintain aerobic conditions and to prevent rapid soil drying, and placed in a controlled environmental chamber in darkness, where the temperature was maintained constant at 25° C.

Two days later, the bottle was removed from the environmental chamber and 50 ml of water and 100 ml of toluene were added. The bottle was then tightly sealed with a lid containing a cellophane liner, and vigorously shaken on a variable speed, reciprocating shaker (Eberbach Corp. Model 6000) set at approximately 200 excursions per minute for one hour. After shaking, the bottle contents were allowed to settle, and a 10 ml aliquot of toluene was transferred by pipette into a glass vial and sealed with a polyseal cap. The toluene extract was analyzed for herbicidal content by gas chromatography. The chromatogram data was then converted to equivalent soil concentrations in parts per million (ppm) by weight of the herbicide.

The results are shown in the table below, where a variety of compounds were tested in two separately treated batches of soil: A control run without an extender compound was conducted for each soil batch, to show how the drop is herbicide concentration was affected by the extender compound. In each case, the quantity of herbicide remaining in the soil after two days was dramatically increased when the extender compound was added.

TABLE I

2-DAY SOIL PERSISTENCE DATA

Herbicide: S—Ethyl di-n-propylthiolcarbamate (EPTC) at 6 lb/A (6 ppm in soil)
Extender: As shown at 4 lb/A (4 ppm in soil)

| Extender Compound No. | Structural Formula | EPTC Residue After 2 Days (ppm) | |
|---|---|---|---|
| | | With Extender | Without Extender |
| Soil Batch B: | | | |
| 2 | $(C_2H_5)(i\text{-}C_3H_7O)P(=S)\text{-}SCH_2CH_2SCH_2\text{-}N(\text{phthalimide})$ | 2.25 | 1.32 |
| 3 | $(C_2H_5)(n\text{-}C_4H_9S)P(=S)\text{-}OCH_2\text{-}N(\text{phthalimide})$ | 2.08 | 1.32 |
| 4 | $(C_2H_5)(CH_3S)P(=S)\text{-}N(\text{phthalimide})$ | 3.98 | 1.32 |
| 6 | $(C_2H_5)(n\text{-}C_3H_7S)P(=S)\text{-}N(\text{phthalimide})$ | 2.78 | 1.32 |
| Soil Batch C: | | | |

TABLE I-continued

2-DAY SOIL PERSISTENCE DATA

Herbicide: S—Ethyl di-n-propylthiolcarbamate (EPTC) at 6 lb/A (6 ppm in soil)
Extender: As shown at 4 lb/A (4 ppm in soil)

| Extender Compound No. | Structural Formula | EPTC Residue After 2 Days (ppm) With Extender | Without Extender |
|---|---|---|---|
| 7 | n-C$_4$H$_9$O\\P(=S)—SCH$_2$—N(phthalimide)/n-C$_4$H$_9$O | 3.50 | 0.22 |

EXAMPLE 1

Bioassay Results

Compounds having formulas as delineated in the Table of Compounds (Table II) were tested by the procedures below.

TABLE II

TABLE OF COMPOUNDS $$\begin{array}{c} R^4 \\ \phantom{R^4}\diagdown \overset{S}{\underset{\parallel}{\phantom{P}}} \\ \phantom{R^4R^4}P{-}(X{-}R^6)_n{-}N \\ R^5 \diagup \end{array} \begin{array}{c} O \\ \parallel \\ C \\ \diagup \phantom{X}\diagdown \\ \phantom{XXX}R^7 \\ \diagdown \phantom{X}\diagup \\ C \\ \parallel \\ O \end{array}$$

| Extender Cmpd. No. | R$^4$ | R$^5$ | X | R$^6$ | n | R$^7$ |
|---|---|---|---|---|---|---|
| 2 | C$_2$H$_5$ | i-C$_3$H$_7$O— | S | —C$_2$H$_4$SCH$_2$— | 1 | phenyl |
| 3 | C$_2$H$_5$— | n-C$_4$H$_9$S— | O | —CH$_2$— | 1 | phenyl |
| 4 | C$_2$H$_5$ | CH$_3$S— | — | — | 0 | phenyl |
| 6 | C$_2$H$_5$— | C$_3$H$_7$S— | — | — | 0 | phenyl |
| 8 | i-C$_4$H$_9$O— | i-C$_4$H$_9$O— | S | —CH$_2$— | 1 | phenyl |
| 9 | C$_2$H$_5$O— | C$_2$H$_5$O— | O | 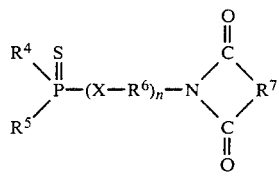 (p-phenylene) | 1 | phenyl |

TABLE II-continued
TABLE OF COMPOUNDS

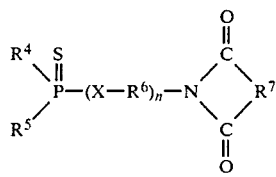

| Extender Cmpd. No. | $R^4$ | $R^5$ | X | $R^6$ | n | $R^7$ |
|---|---|---|---|---|---|---|
| 10 | $C_2H_5-$ | $CH_2=CHCH_2S-$ | — | — | 0 |  |

TEST PROCEDURES WITH ANTIDOTE

This example offers herbicidal activity test data for many representative extender compounds within the scope of this invention showing their effectiveness in improving the herbicidal activity of thiocarbamates. The effect is observed by comparing the extent of weed control in test flats treated with a thiocarbamate against that occurring in similar flats treated with both the thiocarbamate and the extender. The soil used in these tests was a sandy loam soil from Sunol, Calif., which was pre-treated with the herbicide to simulate a typical field which had received previous herbicide applications.

A. Soil Pre-Treatment

The soil was pre-treated in each instance at 3 lb/A. Where the thiocarbamate tested was S-ethyl N,N-diisobutylthiocarbamate, a 6.7 lb/gal (85.2%) emulsifiable liquid concentrate in a 24:1 ratio with the antidote N,N-diallyl-2,2-dichloroacetamide was employed. Where the thiocarbamate was S-propyl N,N-dipropylthiocarbamate, the soil was pretreated with either an emulsifiable liquid concentrate in a 12:1 ratio with the antidote N,N-diallyl-2,2-dichloroacetamide or an emulsifiable liquid concentrate of the herbicide alone. In each instance, the emulsifiable liquid concentrates were diluted in 200 ml of water, such that the resulting concentration of herbicide in the solution was 2000 mg/l. Two hundred ml of this solution was then added to 200 lb (90.8 kg) of soil to which 17-17-17 fertilizer (N-$P_2O_5$-$K_2O$ on a weight basis) had been previously added to a concentration of 50 ppm by weight with respect to the soil. The mixture was mixed in a rotary mixer for 10 to 30 minutes.

The soil was then placed in round plastic containers, 7.5 inches (19.0 cm) in diameter by 7.5 inches (19.0 cm) deep. The soil was tamped and leveled with a row marker to impress one row across the width of each container. This row was seeded with watergrass (Echinochloa crusgalli). Sufficient seeds were planted to produce several seedlings. The containers were then placed in a greenhouse maintained at 20° C. to 30° C. and watered daily by sprinkler.

Five weeks after treatment, the soil was allowed to dry out and the plant foliage was removed. The soil was then passed through a 0.25 inch (0.64 cm) screen to remove plant roots and clods. The soil was then treated according to the procedure in (B) below. Where the pre-treatment was with S-propyl N,N-dipropyl thiocarbamate alone the soil was not employed for one or more months, whereas the thiocarbamate plus antidote conditioned soil was then used shortly after pre-treatment.

B. Herbicide Test

Solutions were prepared by diluting those emulsifiable liquid concentrates described above as containing the antidote N,N-diallyl-2,2-dichloroacetamide and thiocarbamate in 650 ml of water such that the resulting concentration of herbicide in the solution was 1.48 mg/ml. Five ml of this solution when added to three pounds of soil yielded a quantity in the soil equivalent to three pounds per acre.

The extender compounds were used in technical form. These materials were added to 5 ml acetone and 21 ml water such that the resulting concentration of the extender in the solution was 1.54 mg/ml. The acetone contained 1% of an emulsifier/surfactant. Five ml of this solution when added to three pounds of soil yielded a quantity in the soil equivalent to four pounds per acre.

Five ml of the extender solution and 5 ml of the herbicide solution were tank-mixed. The resultant mixture of 10 ml was then added to 3 lbs of soil and incorporated into the soil by a rotary mixer. Thus, 10 ml of the mixture and 3 pounds of soil were placed in rotary mixer and incorporated.

The treated soil was then placed in aluminum flats which were approximately 2.5 inches deep, 3.5 inches wide, and 7.5 inches long. The soil was tamped and leveled with a row maker to impress six rows across the width of the flat. The test weeds were as follows:

| COMMON NAME | ABBREVIATION | SCIENTIFIC NAME |
|---|---|---|
| watergrass | WG | Echinochloa crusgalli (L.) |
| wild oats | WO | Avena fatua (L.) |
| wild cane | WC | Sorghum bicolor (L.) Moench |

R-10 milo (Sorghum bicolor) was also used as a plant growth indicator. Two rows of watergrass were planted. One row of each of the other weeds and plant growth indicator were planted.

Sufficient seeds were planted to produce several seedlings per inch in each row. The flats were then placed in a greenhouse maintained at 70° to 85° F. (21° to 30° C.) and watered daily by sprinkler.

Sixteen days after treatment, the degree of weed control and corn injury were estimated and recorded as a percentage compared to the growth of the same species in a check flat of the same age which had been seeded in conditioned soil but not treated with either an herbicide or an extender. The rating scale ranges from 0 to 100%, where 0 equals no effect with plant growth equal to the untreated check, and 100 equals complete kill.

The compounds tested in this manner are listed in Table II (Table of Compounds) with their structures. An asterisk in the Table indicates that the treatment was run in soil pre-treated with the thiocarbamate S-propyl N,N-dipropyl thiocarbamate, alone, that is, without an antidote. The results are listed in Table III.

The average percentage of weed control is the average for the above-identified weed species and plant growth indicator. Control experiments (herbicide alone with no extender present) were included in each batch for comparison. Substantial improvements in average percent weed control over the control experiments are evident. The herbicidal efficacy of the thiocarbamate three weeks after application was much improved by the use of the extender.

TABLE III

HERBICIDAL ACTIVITY TESTS

Herbicide A: S—propyl N,N—dipropyl thiocarbamate in a 12:1 weight ratio with the antidote N,N—diallyl-2,2-dichloroacetamide
Herbicide B: S—ethyl N,N—diisobutyl thiocarbamate in a 24:1 weight ratio with the antidote N,N—diallyl-2,2-dichloroacetamide
Extender: Indicated by Compound No. (see Table I)
Herbicide Application Rate: 3 lb/Acre
Extender Application Rate: 4 lb/Acre

| Treatment | | Average % Control |
|---|---|---|
| Herbicide | Extender | of 4 Grass Species |
| A (average of 3 trials) | — | 19 |
| A (average of 3 trials) | — | 15* |
| A | 2 | 46 |
| A | 3 | 48 |
| A | 4 | 31 |
| A | 6 | 66* |
| A | 8 | 50* |
| A | 9 | 61 |
| A | 10 | 53 |
| B (average of 3 trials) | — | 6 |
| B | 2 | 24 |
| B | 3 | 45 |
| B | 4 | 58 |
| B | 6 | — |
| B | 8 | — |
| B | 9 | 9 |
| B | 10 | 93 |

TEST PROCEDURES WITHOUT ANTIDOTE

The same procedures were followed as stated above under procedure with antidote supra except that no antidote is present in the emulsifiable liquid concentrates with the thiocarbamates—S-ethyl N,N-diisobutyl thiocarbamate (77.3% active ingredient) and S-propyl N,N-dipropyl thiocarbamate (89% active ingredient); and except that the rating was taken twenty-two days after treatment.

TABLE IV

HERBICIDAL ACTIVITY TESTS

Herbicide A: S—propyl N,N—dipropyl thiocarbamate
Herbicide B: S—ethyl N,N—diisobutyl thiocarbamate
Extender: Compound No. 3 (see Table I)
Herbicide Application Rate: 3 lb/Acre
Extender Application Rate: 2 or 4 lb/Acre

| Treatment | | Extender | Average % Control |
|---|---|---|---|
| Herbicide | Extender | Application Rate | 4 Grass Species |
| A (average of 3 trials) | — | — | 18 |
| A | 9 | 2 | 50 |
| A | 9 | 4 | 63 |
| A | 10 | 2 | 54 |
| A | 10 | 4 | 60 |
| B (average of 3 trials) | — | — | 31 |
| B | 9 | | 48 |
| B | 9 | | 56 |
| B | 10 | | 55 |
| B | 10 | | 53 |

METHODS OF APPLICATION

The herbicidal compositions of the present invention are useful in controlling the growth of undesirable vegetation by pre-emergence or post-emergence application to the locus where control is desired, including pre-plant and post-plant soil incorporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. Dusts

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anticaking and antistatic agents. The particle size of the carrier is usually in the range of 30 to 50 microns.

B. Emulsifiable Concentrates

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. Granules and Pellets

Granules and pellets are physically stable, particulate compositions containing the active ingredients adhering to or distributed through a basic matrix of a coherent, inert carrier with macroscopic dimensions. A typical particle is about 1 to 2 millimeters in diameter. Surfactants are often present to aid in leaching of the active ingredient from the granule or pellet.

The carrier is preferably of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15–30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. Microcapsules

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. In General

Each of the above formulations can be prepared as a package containing both the herbicide and the extender together with the other ingredients of the formulation (diluents, emulsifiers, surfactants, etc.). The formulations can also be prepared by a tank mix method, in which the ingredients are obtained separately and combined at the grower site. The herbicide and extender may both be used in the same type of formulation or a different formulation may be used for each, e.g. the herbicide may be in microcapsule form while the extender may be an emulsifiable concentrate, or vice versa.

As a further alternative, the herbicide and extender can be applied sequentially, with either being applied first. This is a less preferred method, however, since more effective results are obtained with simultaneous application.

In general, any conventional method of application can be used. The locus of application can be soil, seeds, seedlings, or the actual plants, as well as flooded fields. Soil application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide/extender compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide/extender composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed:

1. An herbicidal composition comprising
   (a) an herbicidally effective amount of a thiolcarbamate having the formula $$R^1-S-\underset{\underset{O}{\|}}{C}-N\underset{R^3}{\overset{R^2}{\diagup}}$$

in which $R^1$, $R^2$, and $R^3$ are independently $C_2$–$C_4$ alkyl with the proviso that wherein $R^1$ is ethyl and $R^2$ is propyl, $R^3$ is other than propyl; and
   (b) an amount of an organophosphorus compound sufficient to extend the soil life of said thiolcarbamate, said organophosphorus compound having the formula $$\underset{R^5}{\overset{R^4}{\diagdown}}\underset{\|}{\overset{S}{P}}-(X-R^6)_n-N\diagdown\overset{\overset{O}{\|}}{\underset{\underset{O}{\|}}{C}}\diagup R^7$$

in which
   $R^4$ is selected from the group consisting of $C_1$–$C_4$ alkyl and $C_1$–$C_4$ alkoxy;
   $R^5$ is selected from the group consisting of $C_1$–$C_4$ alkoxy, $C_1$–$C_4$ alkylthio, and $C_2$–$C_4$ alkenylthio;
   $R^6$ is selected from the group consisting of phenyl, $C_1$–$C_4$ alkylene, and $C_2$–$C_4$ alkylthioalkylene;
   $R^7$ is either phenyl or cyclohexenyl;
   X is oxygen or sulfur, and
   n is zero or one,
   with the proviso that wherein $R^4$ and $R^5$ are each ethoxy, $R^6$ is phenyl, X is oxygen and n is one, the thiocarbamate is other than S-ethyl N,N-diisobutyl thiocarbamate.

2. An herbicidal composition according to claim 1 wherein
   $R^4$ is $C_1$–$C_2$ alkyl or $C_2$–$C_4$ alkoxy;
   $R^5$ is $C_2$–$C_4$ alkoxy, $C_1$–$C_4$ alkylthio, or $C_3$–$C_4$ alkenylthio;
   $R^6$ is phenyl, $C_1$–$C_2$ alkylene, and $C_2$–$C_4$ alkylthioalkylene; and
   $R^7$ is phenyl or 3,4-cyclohexenyl.

3. An herbicidal composition according to claim 2 wherein
   $R^4$ is ethyl, ethoxy or isobutoxy;
   $R^5$ is ethoxy, isopropoxy, isobutoxy, methylthio, n-propylthio, n-butylthio, or allylthio; and
   $R^6$ is methylene, phenyl or —$CH_2CH_2SCH_2$—.

4. An herbicidal composition according to claim 3 wherein the thiocarbamate is S-ethyl N,N-diisobutyl thiocarbamate and the organophosphorus compound has the formula

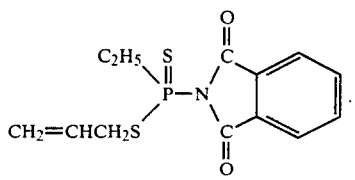

5. An herbicidal composition according to claim 3 wherein the thiocarbamate is S-propyl N,N-dipropyl thiocarbamate and the organophosphorus compound has the formula

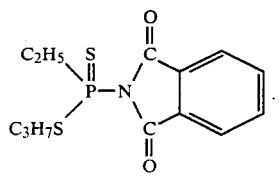

6. An herbicidal composition according to claim 1 in which the weight ratio of thiocarbamate compound to organophosphorus compound is from about 1:1 to about 5:1.

7. An herbicidal composition according to claim 1 further comprising a non-phytotoxic antidotally effective amount of either N,N-diallyl dichloroacetamide or 2,2,5-trimethyl-N-dichloroacetyl oxazolidine.

8. An herbicidal composition according to claim 7 whrein the thiocarbamate is either S-ethyl, N,N-diisobutyl thiocarbamate or S-propyl N,N-dipropyl thiocarbamate and the antidote is N,N-diallyl dichloroacetamide.

9. An herbicidal composition according to claim 7 wherein the weight ratio of said thiocarbamate herbicide to said antidote is from about 3:1 to about 25:1.

10. A method of controlling undesirable vegetation comprising applying to the locus where control is desired both (a) an herbicidally effective amount of a thiolcarbamate having the formula

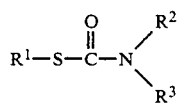

in which $R^1$, $R^2$, and $R^3$ are independently $C_2$-$C_4$ alkyl with the proviso that wherein $R^1$ is ethyl and $R^2$ is propyl, $R^3$ is other than propyl; and (b) an amount of an organophosphorus compound sufficient to extend the soil life of said thiolcarbamate, said organophosphorus compound having the formula

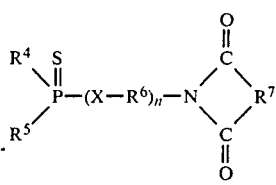

in which
$R^4$ is selected from the group consisting of $C_1$-$C_4$ alkyl and $C_1$-$C_4$ alkoxy;
$R^5$ is selected from group consisting of $C_1$-$C_4$ alkoxy, $C_1$-$C_4$ alkylthio, and $C_2$-$C_4$ alkenylthio;
$R^6$ is selected from the group consisting of phenyl, $C_1$-$C_4$ alkylene, and $C_2$-$C_4$ alkylthioalkylene;
$R^7$ is either phenyl or cyclohexenyl;
X is oxygen or sulfur, and
n is zero or one,
with the proviso that wherein $R^4$ and $R^5$ are each ethoxy, $R^6$ is phenyl, X is oxygen and n is one, the thiocarbamate is other than S-ethyl N,N-diisobutyl thiocarbamate.

11. A method of extending the soil life of a thiocarbamate having the formula

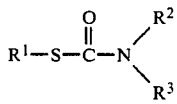

in which $R^1$, $R^2$, and $R^3$ are independently, $C_2$-$C_4$ alkyl with the proviso that wherein $R^1$ is ethyl and $R^2$ is propyl, $R^3$ is other than propyl which comprises applying to the soil containing said thiocarbamate or to which said thiocarbamate is to be applied an effective amount of an organophosphorus compound having the formula

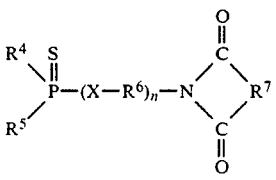

in which
$R^4$ is selected from the group consisting of $C_1$-$C_4$ alkyl and $C_1$-$C_4$ alkoxy;
$R^5$ is selected from the group consisting of $C_1$-$C_4$ alkoxy, $C_1$-$C_4$ alkylthio, and $C_2$-$C_4$ alkenylthio;
$R^6$ is selected from the group consisting of phenyl, $C_1$-$C_4$ alkylene, and $C_2$-$C_4$ alkylthioalkylene;
$R^7$ is either phenyl or cyclohexenyl;
X is oxygen or sulfur, and
n is zero or one
with the proviso that wherein $R^4$ and $R^5$ are each ethoxy, $R^6$ is phenyl, X is oxygen and n is one, the thiocarbamate is other than S-ethyl N,N-diisobutyl thiocarbamate.

* * * * *